(12) United States Patent
Hinshaw et al.

(10) Patent No.: US 10,495,623 B2
(45) Date of Patent: Dec. 3, 2019

(54) SYSTEM AND METHOD FOR ANALYZING DISSOLVED GAS IN ELECTRICAL INSULATING FLUID

(71) Applicant: Serveron Corporation, Beaverton, OR (US)

(72) Inventors: John Hinshaw, Portland, OR (US); Steven Mahoney, McMinnville, OR (US); Thomas Waters, Redmond, OR (US)

(73) Assignee: Serveron Corporation, Beaverton, OR (US)

( * ) Notice: Subject to any disclaimer, the term of this patent is extended or adjusted under 35 U.S.C. 154(b) by 0 days.

(21) Appl. No.: 15/352,483

(22) Filed: Nov. 15, 2016

(65) Prior Publication Data

US 2018/0088101 A1    Mar. 29, 2018

Related U.S. Application Data

(60) Provisional application No. 62/255,587, filed on Nov. 16, 2015.

(51) Int. Cl.
*G01N 33/28* (2006.01)
*G01N 33/00* (2006.01)

(52) U.S. Cl.
CPC ..... *G01N 33/2841* (2013.01); *G01N 33/0014* (2013.01); *G01N 33/0073* (2013.01)

(58) Field of Classification Search
CPC ........... G01N 33/2841; G01N 33/0014; G01N 33/0073
USPC ....................................... 73/19.12
See application file for complete search history.

(56) References Cited

U.S. PATENT DOCUMENTS

| 4,610,169 A * | 9/1986 | Clavell, Jr. ........ G01N 33/1826 422/88 |
| 2012/0222554 A1 * | 9/2012 | Leta .................... B01D 53/0438 95/104 |
| 2012/0304734 A1 * | 12/2012 | Takamoto .......... G01N 33/2841 73/19.11 |

OTHER PUBLICATIONS

Li, Selective Gas Adsorption and Separation in Metal-organic Frameworks, Mar. 2009, Chemical Society Reviews.*

* cited by examiner

*Primary Examiner* — Eric C. McCall
*Assistant Examiner* — Timothy P Graves
(74) *Attorney, Agent, or Firm* — Seed Intellectual Property Law Group LLP

(57) ABSTRACT

A gas analysis system for analyzing dissolved gas in electrical insulating fluid includes a trap that selectively captures or releases one or more gases, a temperature control device for controlling a temperature of the trap that determining whether the trap is in a gas capture mode or a gas release mode, and a gas sensor for analyzing the gas that was not selectively captured by the trap. The trap may be heated to a first temperature that enables the gas to be adsorbed by the trap, and the trap may be heated to a second temperature that enables the gas to be desorbed by the trap. The gas analysis system may further include a gas flow diverter for directing gas flow past the trap. The captured or released gases may be interfering matrix gases. A method and analyzer for analyzing dissolved gas in an electrical insulating fluid are also disclosed.

20 Claims, 2 Drawing Sheets

SYSTEM AND METHOD FOR ANALYZING DISSOLVED GAS IN ELECTRICAL INSULATING FLUID

This application relates to and claims priority of U.S. provisional patent application Ser. No. 62/255,587 filed Nov. 16, 2015, which application is incorporated by reference herein in its entirety for all purposes and this application claims the benefit of that application for all applicable purposes.

FIELD

The present invention relates generally to quantitative analysis of gas mixtures and, more particularly, to a system and method for chemical analysis of gases commonly found dissolved in electrical insulating fluids.

BACKGROUND

Electrical equipment, particularly medium-voltage or high-voltage devices, requires a high degree of electrical and thermal insulation between components thereof. Accordingly, it is well known to encapsulate components of electrical equipment, such as coils of a transformer, in a containment vessel and to fill the containment vessel with a fluid. The fluid facilitates dissipation of heat generated by the components and can be circulated through a heat exchanger to efficiently lower the operating temperature of the components. The fluid also serves as electrical insulation between components or to supplement other forms of insulation disposed around the components, such as cellulose paper or other insulating materials. Any fluid having the desired electrical and thermal properties can be used. Typically, electrical equipment is filled with oil, such as castor oil, mineral oil, or vegetable oil, or synthetic "oil", such as chlorinated biphenyl or silicone.

Often, electrical equipment is used in a mission-critical environment in which failure can be very expensive, or even catastrophic, because of a loss of electric power to critical systems. In addition, failure of electrical equipment ordinarily results in a great deal of damage to the equipment itself and surrounding equipment, thus requiring replacement of expensive equipment. Further, such failure can cause injury to personnel due to electric shock, fire, or explosion. Therefore, it is desirable to monitor the status of electrical equipment to predict potential failure of the equipment through detection of incipient faults and to take remedial action through repair, replacement, or adjustment of operating conditions of the equipment. Faults and incipient faults should be distinguished from normal and acceptable degradation. However, the performance and behavior of fluid-filled electrical equipment inherently degrades over time. Transformer oil cools the transformer and acts as a dielectric. As transformer oil ages it becomes a less effective dielectric. Oil condition also is affected by the condition of other active components in the electrical equipment with which it is in intimate contact.

A method of monitoring the status of fluid-filled electrical equipment is to monitor various parameters of the fluid. For example, the temperature of the fluid and the total combustible gas (TCG) in the fluid is known to be indicative of the operating state of fluid-filled electrical equipment. Therefore, monitoring these parameters of the fluid can provide an indication of any incipient faults in the equipment. For example, it has been found that carbon monoxide and carbon dioxide increase in concentration with thermal aging and degradation of cellulosic insulation in electrical equipment. Hydrogen and various hydrocarbons (and derivatives thereof such as acetylene and ethylene) increase in concentration due to hot spots caused by circulating currents and dielectric breakdown such as corona and arcing. Concentrations of oxygen and nitrogen indicate the quality of the gas pressurizing system employed in large equipment, such as transformers. The measurement of certain gases, such as hydrogen, acetylene, methane, ethane, and ethylene in the oil of an electrical transformer is of interest as it is an indication of the breakdown of the oil caused by overheating and/or arcing inside the transformer. The increase in hydrogen, for example, dissolved in the transformer oil is an indicator of the coming failure of the transformer. Accordingly, "dissolved gas analysis" (DGA) has become a well-accepted method of discerning incipient faults in fluid-filled electric equipment.

In conventional DGA methods, an amount of fluid is removed from the containment vessel of the equipment through a drain or other fluid sampling valve. The removed fluid is then subjected to testing for dissolved gas in a lab or by equipment in the field. This method of testing is referred to herein as "offline" DGA. Since the gases are generated by various known faults, such as degradation of insulation material or other portions of electric components in the equipment, turn-to-turn shorts in coils, overloading, loose connections, or the like, various diagnostic theories have been developed for correlating the quantities of various gases in fluid with particular faults in electrical equipment in which the fluid is contained. If analysis is conducted off site, results may not be obtained for several hours. Incipient faults may develop into failure of the equipment over such a period of time.

Often it is neither practical nor desirable to conduct offline DGA analyses frequently enough to detect incipient faults rapidly enough to take remedial action in a timely manner. Such sampling and testing requires deployment of personnel to a remote site of the monitored electrical asset, which often involves significant time and travel. Customary offline DGA testing intervals range from weeks to years in duration.

Accordingly, in order to acquire DGA analysis results more frequently for critical electrical assets, devices for DGA analysis directly at the transformer have been deployed. Such analysis systems, termed "online" DGA analyzers, are connected directly to the fluid tank of a transformer via a sealed circulation loop. The dielectric fluid flows directly from and back to the tank. This arrangement has the advantage that errors from manual oil sampling are eliminated; fault gases are not lost from the sample during sampling, transport, and lab analysis, and the fault gas content of the oil sample is preserved. The time between oil sample acquisition and analysis in an online system is a matter of minutes, compared to hours or days for offline DGA testing.

Online DGA analyzers utilize a number of analytical chemical technologies including gas chromatography (GC), infrared (IR) spectroscopy, and solid-state sensors. Chromatographic and spectroscopic sensing systems generally require a gas-phase sample from the dielectric fluid, while solid-sensors may respond to a gas-phase sample or directly to gases dissolved in the oil.

Unfortunately, in a spectroscopic gas sensor for process gas analysis, including DGA, the presence of some commonly found matrix gases, such as propane and propylene, interfere with measurement of the analyte gases such as methane, ethane, and ethylene. The interferences arise when the selected radiation wavelengths of the spectroscopic sensor are absorbed by both analyte and matrix gases in common. The interference results in significantly higher sensor readings than the true analyte gas levels, which degrades analyte gas measurement accuracy and repeatability.

Devices such as the GE-Kelman Transfix and related online spectroscopic DGA monitors attempt to address the above problems. In particular, such devices extract dissolved gases from electrical insulating fluids for subsequent analysis. The problem of matrix gas interference is addressed by measuring the aggregate contribution of the interfering and analyte gases together followed by removal of the analyte gases from the contained gas and oil volumes by sparging the oil volume with ambient air and releasing the gases to an outside vent. The analyte gases are less soluble in the oil and are sparged out more rapidly than are the more soluble interfering matrix gases, which are retained preferentially inside the oil volume.

A series of gas-sensor readings is made as the analyte gases are sparged, preferentially from the system wherein the matrix gas concentrations decrease more slowly than the analyte gas concentrations. Ultimately only a small fraction of the analyte gases remain in the system such that the gas sensor measures the fractional remaining analyte gases plus the much larger fraction of remaining matrix gases. Finally, an estimate is calculated of the difference between the gas sensor reading with and without the interfering matrix gases by curve-fitting and extrapolation towards the eventual sensor readings with zero remaining analyte gases and fractional remaining matrix gases. This difference is taken as the sensor reading as if no matrix gases were present.

The rates of removal of the analyte and matrix gases from the electrical insulating fluid sample are primarily a function of their solubility in the fluid. Unfortunately, site-to-site and time-based variations in the chemical nature of the fluid preclude exact knowledge of the degree of partial removal of the gases from the fluid. Subtraction of the extrapolated value of the matrix-gas-only sensor response from the initial full-sample sensor response incurs a large error as well. These uncertainties degrade the ultimate accuracy and repeatability of the analytical results.

In addition, higher molecular weight substances are present in electrical insulating oil, such as hexanes, heptanes, octanes, and so on up to carbon numbers in excess of $C_{40}$ and higher in the case of mineral insulating oil. At normal oil operating temperatures from 20 to 100° C. the more volatile of these oil components will partially vaporize. The vaporized oil matrix substances may then condense on sufficiently cool surfaces to which they are exposed, as in for example the gas paths leading to a spectroscopic sensor and inside the sensor itself. Having condensed in the active spectroscopic sensing area, these less volatile, condensed matrix compounds can interfere with the measurement of the analyte gases in much the same way as gaseous matrix components.

Existing on-line DGA devices achieve some remediation of condensing matrix vapors by establishing and maintaining a positive thermal gradient between the bulk oil sample temperature and the gas analyzer. In this manner, accumulation of condensable matrix compounds may be minimized but not entirely eliminated.

SUMMARY

In order to provide a system having improved quantitative analysis of gas mixtures that consist of gases of interest (analyte gases) plus other gases present (sample matrix gases), the new and novel system described herein provides substance-specific trapping and removal of interfering matrix gases from a sample gas stream or volume for chemical analysis of gases commonly found dissolved in electrical insulating fluids, dissolved gas analysis (DGA), in a multi-step process. Advantageously, because matrix gases may interfere with the measurement of the analyte gases so as to degrade the accuracy, precision, and repeatability—the quality of results—of the analyte gas measurements, removal of interfering matrix gases from a gas sample improves the results quality by reducing or eliminating such interferences.

The physicochemical basis for the present system is found in a well-known area of separation science that involves adsorptive trapping and desorptive release of chemicals for monitoring, purification, and bulk separation. Such separations are achieved by (1) establishing conditions for differential adsorption of two or more substances on an adsorptive material; (2) exposing the substances to the adsorptive material either in bulk or by flow through a defined bed; (3) separating the adsorptive material that contains the adsorbed substances from the non-adsorbed substances; and (4) adjusting the chemical and/or physical conditions of the adsorptive material so as to change the affinity of adsorbed substances such that they are released from the adsorptive material. Such adjustments may be enacted by thermal, pressure, or chemical solubility cycles.

The system includes a gas sensor; a selective-adsorption gas trap; a device to create a pressure differential across, and corresponding flow through, the gas trap; a stream-switching device to isolate or include the sensor in the gas flow and to reverse gas flow through the gas trap; and a means for heating the gas trap intermittently. Gas sample may be provided from a static gas sample volume or a flowing gas sample stream. An additional purge gas source free of the analyte and the interfering matrix gases may be provided as well.

Optionally, the system may also include an additional clean gas source for trap scrubbing after each analysis cycle; gas flow switching to divert flow around the gas sensor and to reverse flow through the trap; a pressure transducer to monitor the pressure drop across the adsorptive trap.

Thus, it can be seen that the new and novel system is able to compensate for the effects of interfering matrix gases in a quantitative gas analyzer, improve the accuracy and repeatability of such compensation by completely removing interfering matrix gases from the gas sample stream while retaining a repeatable fraction of analyte gases without dependence upon the matrix or analyte gases' solubility in the electrical fluid being analyzed, and allow the direct measurement of the analyte gases in the absence of the interfering matrix gases.

BRIEF DESCRIPTION OF THE DRAWINGS

The objects, features, and advantages of the present new and novel system will be apparent from the following detailed description with references to the following drawings.

DETAILED DESCRIPTION

The presently described system is based on a new and novel application of the technique of analytical thermal desorption. Thermal desorption is applied in diverse areas such as air monitoring, polymer analysis, food analysis, breath analysis, and detection of chemical agents for security. However, thermal desorption has never been used to address the problem of matrix gas interference in dissolved gas analysis using spectroscopic gas sensing.

A significant advantage of the newly described system includes the ability to provide accurate and repeatable correction for matrix gas interference by employing well-characterized adsorptive materials for matrix-gas trapping, not depending on the physicochemical characteristics of the fluid under analysis, completely removing interfering matrix gases from the gas sample, retaining a repeatable and measurable fraction of the analyte gases after matrix-gas trapping, and thermally regenerating the adsorptive material post-analysis. Other advantages may be realized as well, as described below.

Figure 1:
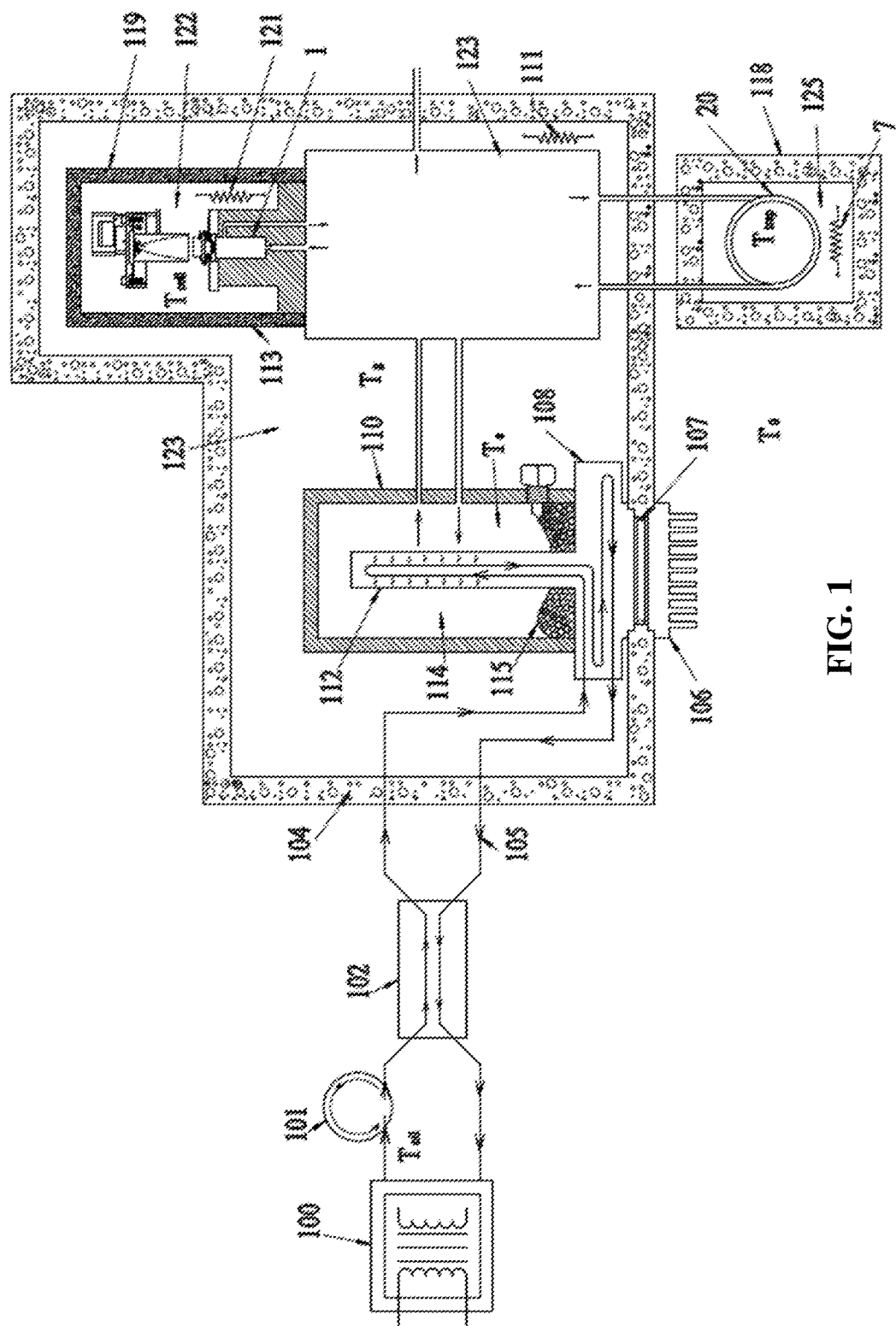
FIG. 1 is a schematic of one exemplary embodiment of an overall analysis system that incorporates the subject thermal desorption system, a source of gases to be analyzed, and thermal control of the components.

As shown in FIG. 1, in the present exemplary embodiment thermal control of the spectroscopic cell is arranged such that the electrical fluid dissolved-gas extractor and the spectroscopic cell temperature may be controlled at operating temperatures that establish a sufficient positive thermal gradient at the spectroscopic cell and effect suppression of condensation of the less volatile matrix components.

In an additional step unique to this newly described system, the spectroscopic cell temperature may be elevated periodically while circulating gas through the cell and the absorptive trap such that condensed compounds in the spectroscopic cell that may evaporate from the cell surfaces are trapped in the first section of the adsorptive trap. After sufficient time has elapsed for the majority of the condensed material to be evaporated from the cell and absorbed in the trap, a trap cleaning cycle, as described above, is initiated and the trap is purged of the adsorbed compounds. It should be noted that these less volatile compounds will be completely trapped in the first, less absorptive, section of the trap.

Once the trap cleaning cycle is complete, the system is returned to its initial state in preparation for continuation of the normal analysis cycles. Such a cell cleaning cycle is initiated as required by the level of cell contamination build-up, which is determined by a background measurement in the absence of analyte compounds. One cycle per day is a practical maximum frequency for cell clean-up cycles; a frequency of one cycle per month represents a practical minimum, although the frequency of cycles may be varied as desired.

Continuing to refer to FIG. 1, an exemplary embodiment of the new and novel thermal desorption system is shown. It includes an oil pump 101, oil circulation path 105, heat exchanger 102 and gas extractor 112. There is also included a gas switching manifold 123, PAS gas measurement apparatus 122 and a chemical trap 20. The system further includes heaters 111, 112, 7 and insulation 118, 104, 110, 113.

In actual operation, beginning at a transformer 100 being monitored, transformer dielectric oil 115 containing fault gases 114 to be analyzed, is circulated via the oil pump 101 along the oil circulation path 105. The oil passes through the counter flow heat exchanger 102 to remove or add heat in the direction of the thermal set point Te of the gas extractor 112.

The system includes four distinct thermal zones. The first thermal zone contains the gas extractor 112 (maintained at Te), the second one contains the gas switching manifold 123 (maintained at Tg), the third one contains the PAS gas measurement apparatus 122 (maintained at Tcell) and the fourth one contains a chemical trap 20 (Ttrap). All zones are independently thermally controlled with heaters 111, 121, 7 and isolated by insulation 118, 104, 110, 113. In addition, the gas extractor thermal set point Te can be bi-directionally controlled with the thermal electric cooler 7, moving the heat from the oil exchanger 8 to the head sink radiator 6 and shed externally to ambient air. The thermal zones temperatures are controlled such that as the extracted sample gas sample travels through the system, it is exposed to increasingly higher temperatures. This prevents oil vapor partials contained within the sample from condensing on any of the PAS surfaces walls, windows and such until they have been either returned to the extractor or vented over board.

Figure 2:
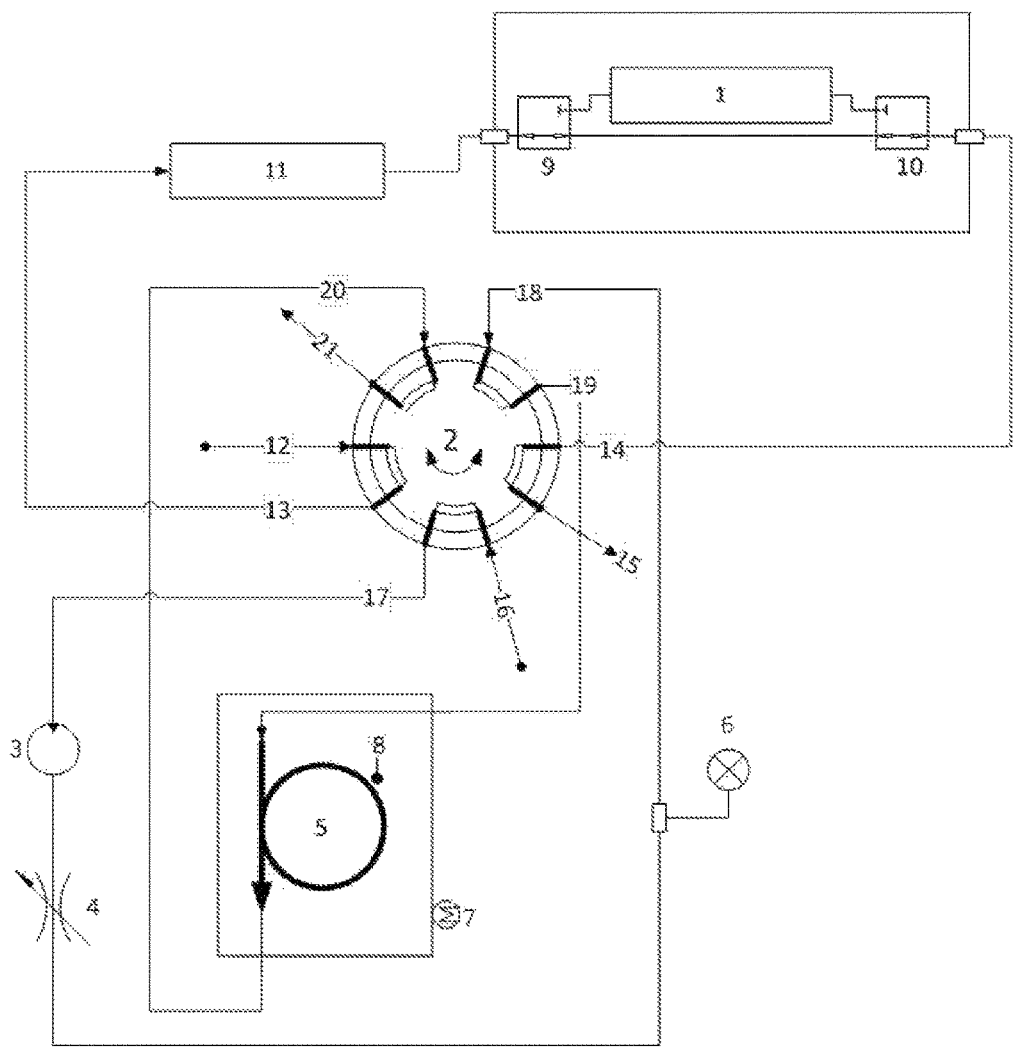
FIG. 2 is an operational schematic of the thermal desorption system in an exemplary embodiment.

Turning now to FIG. 2, there is illustrated an exemplary configuration of the new and novel thermal desorption system directed to photoacoustic absorption spectroscopy (PAS) measurement for dissolved gas analysis (DGA) of electrical insulating fluids.

The system includes an incoming gas stream 12, a gas detection cell 1, a rotary valve 2, a gas pump 3, a variable restriction 4, a tubular trap 5, containing one or more suitable adsorbent materials, a pressure transducer 6, a heating means 7, a temperature sensor 8, two three-way electrical solenoid valves 9, 10, and an additional volume 11.

In operation, in the initial or standby state, sample gas enters the rotary valve at a first connection 12, exits the rotary valve 2 at a second connection 13, flows through a volume 11 to a three-way valve 9. It is then either vented or returns to the sample supply via fourth and fifth connections 14 and 15 on the rotary valve 2. The adsorbent trap 5 is heated to an initial temperature with the heater 7, where that temperature is suitable for the strong adsorption of interfering gases while only weakly adsorbing the analyte gases. By way of example and not limitation, the currently described configuration uses a temperature of 45-65° C.

In a first step (gas purge) of the analysis process, sample gas is diverted through the gas analysis cell 1 by energizing the three-way valves 9, 10. At the same time, the gas pump 3 is energized, drawing purge gas through the rotary valve 2 from the sixth connection 16 to the seventh connection 17. Purge gas is compressed in the pump 3, flows through the restriction 4, past the pressure transducer 6 and enters the rotary valve 2 at the eighth connection 18. Purge gas exits the rotary valve 2 at the ninth connection 19 and enters the adsorbent trap 5. Purge gas flows through the adsorbent trap 5 under impetus of the pressure drop created by the gas pump across the particulate packing contained therein, flows through the trap 5 and enters the rotary valve 2 at the tenth connection 20. Purge gas exits the rotary valve 2 at the position 21 and is vented. The purpose of this purge gas step is to remove any remaining gases from the trap and tubing prior to starting the adsorption of interfering gases in step 3. The flow rate through the trap 5 may be adjusted with the variable restrictor 4, and the pressure drop across the trap 5 may be observed via the pressure transducer 6. The measured flow rate in this exemplary configuration is 15-22 mL/min, depending on the trap temperature (gas viscosity increases as temperature increases).

In step 2 (gas measurement I) of the analysis process, the first three-way valve 9, and approximately 1 second later the second three-way valve 10, are de-energized, thereby pneumatically isolating the gas measurement cell 1 while bringing its internal pressure to equal ambient pressure. The gas pump 3 is de-energized, causing the pressure drop across the trap 5 to decay to zero and flow through it to cease after a delay. One or more gas measurements are performed at this time in the gas measurement cell 1. Gas measurements of non-interfered-with gases are complete at this stage. Measurements of interfered-with gases are subsequently performed after removal of interfering gases in the next steps.

In Step 3 (interfering gas removal) of the analysis process, after initial gas measurement has been completed, the three-way valves 9, 10 are energized. The rotary valve 2 is actuated to its alternate position causing connection 13 to communicate with position 17, 16 with 15, 14 with 19, 18 with 20, and 21 with 12. The gas pump 3 is energized and sample gas plus entrained purge gas are mixed and circulated from the measurement cell 1 through the volume 11, the gas pump 3, the restriction 4, the adsorbent trap 5, and back into the measurement cell 1. The adsorbent material in the trap 5 selectively retains up to one hundred percent of interfering matrix gases while passing through up to one hundred percent of analyte gases. The sample gas is diluted with the purge gas in the entirety of the volume contained in the communicating portions of the system. In addition, the circulating concentrations of the fully adsorbed matrix gases are reduced to nearly zero, while the circulating concentrations of the analyte gases are reduced in proportion to the degree of adsorption of the individual gases onto the adsorptive material in the trap 5 at its current temperature. The concentrations of gases in the gas stream will reach a steady state after multiple rounds of circulation through the trap 5. The adsorption of interfering matrix gases on the trap 5 must be sufficient so that the interfering gases do not break through the trap and re-enter the analytical gas stream during gas circulation.

In step 4 (gas measurement II), the gas pump 3 is de-energized and gas flow through the trap 5 decays to zero as the pressure at the transducer 6 approaches a steady state approximately equal to or greater than local ambient pressure. At or before achieving ambient pressure, the three-way valves 9, 10 are de-energized and the rotary valve 2 is actuated to its original position. The first three-way valve 9 is momentarily energized such that the pressure in the gas measurement cell 1 becomes equal to ambient pressure. With the first three-way valve 9 closed again, additional gas measurements are performed in the gas cell 1. The concentrations measured in this second series of gas measurements reflect analyte gas concentrations after dilution with purge gas and passage through the trap 5. The original gas concentrations may be calculated using equation 1.

There exists an optimum time and gas volume flow through the trap such that the circulating analyte gas concentrations reach maximum values after gas circulation begins. This maximum concentration time, $t_{max}$ is characteristic of the flow rate, trap temperature, trap material, and total volume of the communicating portions of the gas circulation. In the current configuration $t_{max} \approx 120$ s. The achieved gas concentrations are a function of the degree of sample dilution with purge gas and the strength of adsorption of individual gases in the trap 5:

$$c_g^o = \frac{c_{meas} k_g}{f_{dil}} \quad (1)$$

where $c_g^o$ is the original gas measurement as without interference, $c_{meas}$ the measured gas concentration of gas g upon completion of this trapping step, $f_{dil}$ is the dilution factor or volumetric ratio of the sample and purge gas volumes, and $k_g$ is a frontal adsorption coefficient of gas g on the trap 5. The $f_{dil}$ coefficient can be calculated as:

$$f_{dil} = \frac{V_A}{V_T} \quad (2)$$

where $V_A$ is the gas volume of the analysis portion of the system shown in FIG. 1 (i.e. the sum of the volumes of the sensor 1 plus the additional volume 11 plus the interconnecting tubing and communicating valve 2 volumes, and $V_T$ is the total gas volume of the system including $V_A$ plus the pump 3, the trap 5, the pressure sensor 6 and related interconnecting tubing and communicating the valve 2 volumes. The dilution factor $f_{dil}$ can be maximized towards 1.0 by increasing the additional volume 11 and decreasing the trap 5 volume. However this adjustment is limited by the corresponding increase in the volume of sample gas required. The dilution factor can be measured by performing this described procedure using a pure gas sample with no interfering matrix gases and with the trap 5 in a heated condition such that adsorption of the (single) pure gas in the sample does not affect its concentration significantly. The dilution factor is then:

$$f_{dil} = \frac{c_g}{c_g^o} \quad (3)$$

where $c_g$ is the measured single-gas concentration after the heated trap is introduced into the gas stream.

The frontal adsorption coefficient $k_g$ is a function of the trapping temperature, amount of adsorbent present, and adsorptivity of the gas on the adsorbent bed. It can be approximated from frontal chromatographic measurements for individual gases or directly from a trapping system by analyzing pure analyte gases without interfering matrix gases but with trapping, as in:

$$k_g = \frac{c_g^o}{c_g^{tr}} \quad (4)$$

Where $c_g^{tr}$ is the measured pure gas concentration after trapping. The adsorption coefficient is also a function of trap temperature, where lower temperatures will cause stronger adsorption of analyte gases thereby increasing $k_g$.

In step 5 (trap cleanup), the three-way valves 9, 10 are de-energized, the rotary valve 2 is actuated to its original position, the pump 3 is energized, and the heater 7 is energized so that the temperature of the trap 5 increases sufficiently to cause the desorption of adsorbed gases from the trap, including both interfering gases and target analytes. In the current configuration, the desorption temperature is 200° C. Trap desorption is made more efficient by reversal of the flow direction, or back-flushing, through the trap 5, such that interfering matrix gases which are preferentially adsorbed at the front of the trap are preferentially desorbed during the cleanup cycle. The temperature of the trap 5 is controlled by appropriate feedback means with the temperature transducer 8. After sufficient time to clear the trap of any residual gases, the heater 7 is deactivated and the system returns to the initial state.

In an alternate configuration of the adsorbent trap, a dual-adsorbent bed is utilized. A first adsorbent section occupies a defined and separate first fraction of the trap volume and a second adsorbent section occupies the remainder of the trap volume in a separately defined area.

The first adsorbent section starts at the entrance to the trap tube that first receives gas sample during Step 3, above. At the initial trap temperature the first adsorbent material is less adsorbing and has a smaller adsorption coefficient $k_g$ for the analyte and interfering matrix gases than the second adsorbent material, but the first adsorbent material does adsorb less volatile, condensable longer-chain hydrocarbons such as $C_7$-$C_{16}$ as well as other trace matrix components in the sample gas that may or may not interfere with the IR analysis of the target gases. Such materials may be present in the dielectric fluid under analysis in significant concentrations, and some fraction of these materials may be released from the dielectric fluid into the gas space undergoing DGA measurement. Such materials may also be released into the circulating gas stream during a PAS cell clean-up thermal cycle such as is described below.

The purpose of the first adsorbent material is to preferentially adsorb such less-volatile matrix components that, if adsorbed on the second more strongly adsorbing material, might not be completely desorbed upon trap heating and flow reversal. The first adsorbing material effectively increases the lifetime, or the number of sequential analysis cycles that may be performed, without depleting the effectiveness of the second adsorbing material for totally adsorbing the more volatile interfering matrix gases such as propane and propylene.

Considering the above described arrangement of spectroscopic analysis cell, gas pump, valving, interconnecting tubing, and thermally controlled trap, an additional spectroscopic cell clean-up thermal cycle can be realized. As previously stated, it is known in the art that less volatile compounds may be transferred through the gas phase by evaporation from a source such as the electrical insulating fluid under test, and such compounds may condense subsequently on the inner surfaces of the spectroscopic analysis cell thereby causing interference with the measurement of analyte substances. Although it has been shown in the prior art that such condensation can be reduced or controlled by establishing a positive thermal gradient from the source of the condensable compounds towards the spectroscopic cell, such an arrangement does not completely stop the condensation and interference. Condensable compounds may build up over an extended period of operation sufficiently to make the spectroscopic cell incapable of detecting analyte compounds with a desired sensitivity.

Although the present new and novel system has been described in terms of specific exemplary embodiments, it will be appreciated that various modifications and alterations might be made by those skilled in the art without departing from the spirit and scope of the invention as set forth in the following claims.

What is claimed is:

1. A gas analysis system for analyzing dissolved gas in electrical insulating fluid, comprising:
    a trap that selectively captures or releases one or more gases depending on a temperature of the trap, wherein when the trap is at a first temperature, the trap operates in a gas capture mode in which the trap captures an interfering gas comprising a C3 hydrocarbon or larger while allowing a gas of interest comprising a C2 hydrocarbon or smaller to pass, and when the trap is at a second temperature different from the first temperature, the trap operates in a gas release mode in which the traps releases the captured interfering gas;
    a temperature control device that controls the temperature of the trap such that the trap is in the gas capture mode or in the gas release mode; and
    a photoacoustic spectrometer that analyzes the gas of interest that was not selectively captured by the trap.

2. The gas analysis system of claim 1, wherein the trap captures the interfering gas using a process of adsorption.

3. The gas analysis system of claim 1, wherein the trap releases the interfering gas using a process of desorption.

4. The gas analysis system of claim 2, wherein the temperature control device causes heating of the trap to the first temperature which causes material in the trap to adsorb the interfering gas.

5. The gas analysis system of claim 3, wherein the temperature control device causes heating of the trap to the second temperature which causes material in the trap to desorb the interfering gas.

6. The gas analysis system of claim 1 further comprising a gas flow diverter that directs gas flow through the trap in a first direction while the trap is in the gas capture mode, and through the trap in a second direction different than the first direction while the trap is in the gas release mode.

7. The gas analysis system of claim 1, wherein the captured interfering gas, if not captured in the trap, interferes with analysis of the gas of interest by the photoacoustic spectrometer.

8. A method for analyzing dissolved gas in an electrical insulating fluid comprising:
    receiving a flow of gas that includes multiple types of gases, wherein one type of gas in the flow of gas is a gas of interest to be measured using photoacoustic absorption spectroscopy (PAS) and another type of gas in the flow of gas is an interfering gas known to interfere with PAS measurement of the gas of interest;
    setting a first temperature of a chemical trap such that the chemical trap is in a gas capture mode of operation;
    directing the flow of gas in a first direction through the chemical trap;
    selectively capturing the interfering gas in the chemical trap while the chemical trap is in the gas capture mode of operation, wherein the gas of interest passes through the chemical trap to a photoacoustic spectrometer for analysis;
    analyzing, by a photoacoustic spectrometer, the gas of interest not selectively captured by the chemical trap;
    setting a second temperature of the chemical trap such that the chemical trap is in a gas release mode of operation; and
    directing gas flow through the chemical trap in a second direction that is different than the first direction while the chemical trip is in the gas release mode of operation, wherein the interfering gas is released from the chemical trap.

9. The method of claim 8, wherein the chemical trap captures the interfering gas using an adsorption process.

10. The method of claim 8, wherein the chemical trap releases the captured interfering gas using a desorption process.

11. The method of claim 9, wherein the adsorption process is controlled by setting the first temperature of the chemical trap to a first predefined value.

12. The method of claim 10, wherein the desorption process is controlled by setting the second temperature of the chemical trap to a second predefined value.

13. The method of claim 8, wherein the gas of interest that is not selectively captured by the chemical trap includes at least one of carbon monoxide, carbon dioxide, acetylene, methane, ethane, or ethylene.

14. The method of claim 8, wherein the interfering gas that is selectively captured and released by the chemical trap includes at least one of C3 hydrocarbons or propanes.

15. The method of claim 10 further comprising after directing gas flow through the chemical trap in the second direction, resetting the chemical trap to the first temperature.

16. An analyzer for analyzing dissolved gas in electrical insulating fluid, comprising:
- a trap that selectively captures one or more interfering matrix gases depending on a temperature of the trap, wherein the trap has a first adsorbent material occupying a first fraction of a volume of the trap and a second adsorbent material occupying a second fraction of the volume of the trap, wherein the first adsorbent material is less adsorbent than the second adsorbent material;
- a temperature control device that controls the temperature of the trap at a first selected temperature, wherein the first selected temperature configures the trap to operate in a gas capture mode;
- a gas sensor that analyzes the gas that was not selectively captured by the trap, enabling the gas sensor to perform direct measurement of an analyte gas substantially in absence of interfering matrix gas; and
- a gas flow diverter that directs gas flow through the trap in a first direction while the trap is in the gas capture mode, and through the trap in a second direction different than the first direction while the trap is in a gas release mode.

17. The analyzer of claim 16, wherein the temperature control device further controls the temperature of the trap at a second selected temperature, wherein the second selected temperature configures the trap to operate in the gas release mode.

18. The analyzer of claim 16, wherein the first selected temperature enables the trap to adsorb the one or more interfering matrix gases.

19. The analyzer of claim 17, wherein the second selected temperature enables the trap to desorb the one or more interfering matrix gases.

20. The analyzer of claim 16, wherein the second direction through the trap is opposite to the first direction.

* * * * *